(12) United States Patent
Zenoni et al.

(10) Patent No.: US 6,255,480 B1
(45) Date of Patent: Jul. 3, 2001

(54) AMINOTHIAZOLE DERIVATIVES USEFUL IN THE PREPARATION OF β-LACTAM ANTIBIOTICS

(75) Inventors: Maurizio Zenoni; Mario Leone; Maurizio Serra; Mauro Filippi, all of Milan (IT)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/331,702

(22) PCT Filed: Nov. 28, 1997

(86) PCT No.: PCT/EP97/06654

§ 371 Date: Jun. 24, 1999

§ 102(e) Date: Jun. 24, 1999

(87) PCT Pub. No.: WO99/23082

PCT Pub. Date: May 14, 1999

(30) Foreign Application Priority Data

Oct. 30, 1997 (IT) .............................................. MI97A2439

(51) Int. Cl.[7] ...................... C07D 277/38; C07D 417/12; C07D 501/06

(52) U.S. Cl. ........................... 540/222; 540/228; 548/170

(58) Field of Search ............................ 548/170; 540/222, 540/228

(56) References Cited

U.S. PATENT DOCUMENTS

| | | | | |
|---|---|---|---|---|
| 4,293,550 | * | 10/1981 | Blumbach et al. | 424/246 |
| 4,703,046 | * | 10/1987 | Ueda et al. | 514/202 |
| 5,003,073 | * | 3/1991 | Ascher | 548/170 |
| 5,411,874 | | 5/1995 | Ellwood et al. | 435/84 |
| 5,654,425 | | 8/1997 | Zenoni et al. | 540/222 |
| 5,869,649 | * | 2/1999 | Khanna et al. | 540/227 |

FOREIGN PATENT DOCUMENTS

| | | | |
|---|---|---|---|
| 0 037 380 | 10/1981 | (EP) | C07D/501/06 |
| 0 055 465 | 7/1982 | (EP) | C07D/501/20 |
| 210 815 | 4/1987 | (EP) | C07D/499/70 |
| WO 97/12890 | 4/1997 | (EP) | C07D/501/22 |
| 96/20198 * | 7/1996 | (WO) . | |
| WO 97/13772 | 4/1997 | (WO) | C07D/501/59 |

* cited by examiner

Primary Examiner—Laura L. Stockton

(57) ABSTRACT

Aminothiazole derivatives having the carboxyl activated by means of thioesters, said derivatives being condensable with β-lactam nuclei to yield β-lactam antibiotics

5 Claims, No Drawings

AMINOTHIAZOLE DERIVATIVES USEFUL IN THE PREPARATION OF β-LACTAM ANTIBIOTICS

Cross Reference to Related Applications

This application is the national stage of application no. PCT/EP97/06654, filed on Nov. 28, 1997, which application claims priority from IT MI97A002439 filed Oct. 30, 1997.

The present invention regards aminothiazole derivatives, and more in particular aminothiazole derivatives with the carboxyl activated by means of thicesters, which may be used for the preparation of β-lactam antibiotics.

β-lactam antibiotics are well known in the literature, and many of them, the cephalosporins, are widely used in medical treatment, whilst many others are still being developed, as described in the literature, for instance in patents WO 97/13772 and No 97/12890.

Also a large number of methods are known for the preparation of aminothiazole cephalosporins (third generation), one of which is described in the aforementioned patent WO 97/13772, where the β-lactam nucleus is condensed with a derivative of the compound having the following formula:

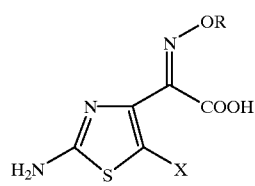

where R is a trityl group and X is a chlorine atom, the definition "derivative" meaning that the compound (II) has the carboxyl activated by means of chloride. The drawback of this condensation system is that it requires a subsequent chromatographic purification phase of the cephalosporin obtained, with a consequent decrease in the yield and increase in production costs.

In addition, in the literature activation processes are described which employ dicyclohexylcarbodiimide (DCC) or DCC/hydroxvbenzotriazole, but these activation processes, besides being very costly, are not suitable for the production of β-lactam antibiotics on an industrial scale.

Patents EP-A-037380 and EP-A-210815 describe other methods of activation on aminothiazole derivatives that are similar to those described by formula (II), but the conversion yields that may be obtained in the condensation with the β-lactam nucleus are low.

Patent U.S. Pat. No. 4,767,852 describes aminothiazole derivatives of compounds of formula (II) in which the activation of the carboxyl group is obtained by means of thioesters; in this formula, however, the meaning of X is in every case exclusively H (hydrogen): when these derivatives are condensed, according to a method described in the patent itself, with a β-lactam nucleus, in all cases cephalosporins or β-lactam antibiotics are obtained in which X is always and exclusively H. Following the teachings of patent U.S. Pat. No. 4,767,852, it is therefore not possible to obtain all β-lactam antibiotics, such as those described in patent WO 97/13772, which are useful against the strains producing β-lactamase (resistant strains) in a similar way as with all other third-generation β-lactam antibiotics having an aminothiazole structure.

The main purpose of the present invention is hence that of producing aminothiazole derivatives that may be condensed with β-lactam nuclei to yield a wide range of β-lactam antibiotics (among which those described in patent WO 97/13772) with high levels of purity and yield.

More in particular, the invention regards aminothiazole derivatives having the formula

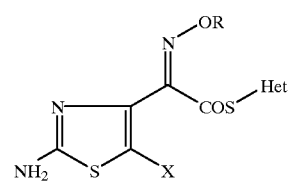

where
X is a halogen, $C_1$–$C_4$ alkyl;
Het is a 5- or 6-term heterocyclic ring having in the ring at least one hetero-atom chosen from the group made up of N, S, 0, either just as it is or condensed with a benzene ring;
R is H, $C_1$–$C_4$ aikyl, —$CH_2$—COOH or $C(CH_3)_2$—COOH, the acid functions of which are free, salified or esterified, $CH_o$—CN, $CH_2CF_3$, $CH_2F$,

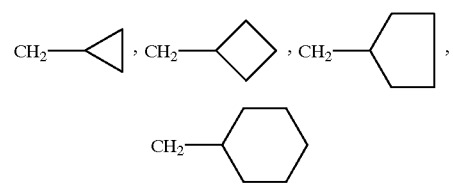

or a protective group of the easily removable type.
Preferably, X is Cl; Het is chosen from among the group consisting of

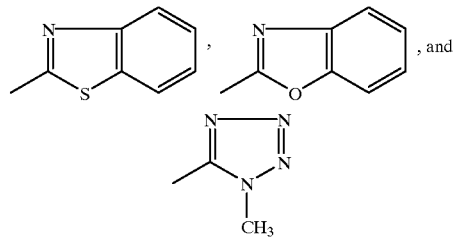

R is chosen from among the group consisting of trityl (Tr), tetrahydropyranyl (THP), tert-butyldimethylsilyl (TBDMS), trimethylsilyl (TMS), and methoxymethyl (MOM).

The derivatives of formula (I) may in turn be easily obtained starting from the corresponding acids (described in patent WO 97/13772) according to the procedure described in patent U.S. Pat. No. 4767852.

The aminothiazole derivatives (I) may be easily condensed with β-lactam nuclei (is necessary, protected) to give β-lactam antibiotics with complete retention of the stereochemistry of the oxime formula C=N—OR (and hence with high levels of purity and high yields).

In particular, it may be noted that the condensation reaction of the derivatives (I) with the β-lactam nuclei may be conducted at temperatures of between −30° C. and +80° C., preferably of between −5° C. and +40° C., using highly polar organic solvents (pure, or mixed together, or mixed with water up to 50% of water, also in two-phase systems) capable of solubilizing (even only partially) the reagents (in particular the derivatives I), such as methylene chloride, ethyl acetate, dimethylformamide, dimethylacetamide, N-methyl-2-pyrrolidone, acetone, dimethyl sulphoxide, methanol, ethanol, isopropanol, and sulpholane, having a high dielectric constant. The examples that follow are illustrative of the present invention.

EXAMPLE 1

Preparation of (Z)-2-aminothiazolyl-5-chloro-α-trityloximino acetate of 2-mercaptobenzothiazolyl To 900 mlit of methylene chloride are added at room temperature 245 g of benzothiazole disulphide and 193 g of triphenylphosphine and, under fast stirring, 355 g of (Z)-2-aminothiazolyl-5-chloro-α-trityloximino acetic acid (273 g of activity)—which is a compound of formula (II) where X is Cl and R is trityl—obtained according to what is described in WO 97/13772. The reaction is exothermic, the temperature rising spontaneously to 35° C. After 10 minutes, the above is left under slow stirring, and the product, as it forms, crystallizes. The reaction is complete in the course of 1 hour (35° C.). At the end of the reaction, cool off to 15° C. and leave under stirring for 1 hour. Filter and wash with 600 mlit of methylene chloride. Dry in a vacuum at 40° C., until constant weight is reached.

In this way, 322 g of the product of formula (I) are obtained in which X is Cl, R is trityl and Het is benzothiazolyl.

Melting point, 170° (decomposition) $^1$H NMR (solvent DMSO D6 ISTD tetramethylsilane) 8.26/8.23 ppm (1H, m); 8.11/8.08 ppm (1H, m); 7.64/7.27 ppm (19H, m).

EXAMPLE 2

Preparation of (Z)-2-aminothiazolyl-5-chloro-α-trityloximino acetate of 2-mercaptobenzothiazolyl The reaction is conducted as in the previous example, except for the fact that 75 g of triethylamine are added in the course of the reaction. In this way, 315 g of product are obtained having the same chemico-physical characteristics.

EXAMPLE 3

Preparation of 7-β-[(Z)-2-aminothiazolyl-5-chloro-α-trityloximino acetamide]-3-chloro-cephalosporanic acid sodium salt Suspend 6 g of 3-Cl-7-amino-cephalosporanic acid in 50 mlit of methylene chloride and protect as trimethylsilyl ester according to procedures described in the literature (Pierce, "Silylation of Organic Compounds", Pierce Chem. Co. Rockford III; J. Am. Chem. Soc. 85, 2497, 1963). Dilute the silylated product with 50 mlit of dimethyl acetamide, add 15 g of thioester obtained as described in the foregoing, example, and leave to react at room temperature overnight. Correct the pH to 6.5 with soda and wash the organic phase with a 10% sodium chloride aqueous solution (80 mlit for five times).

Evaporate the organic phase until an oil is obtained, which is diluted with 100 mlit of isopropanol so as to crystallize the product. Filter and wash with isopropanol.

After drying, 30.5 g are obtained of product having an HPLC purity of 96.7%.

Melting point, 165° (decomposition) $^1$H NMR (solvent DMSO D$_5$ ISTD tetramethylsilane) 9.92/9.89 (1H, d); 7.34/7.19 (17H, m); 6.04/6.00 (1H, dd); 5.32/5.30 (1H, d); 4.02/3.66 (2H, AB)

EXAMPLE 4

Preparation of 7-β-[(Z)-2-aminothiazolyl-5-chloro-α-trityloximino acetamide]-3-chloro-cephalosporanic acid para-nitrobenzyl ester Dissolve 12 g of thioester obtained according to Example 1 or Example 2 in 130 mlit of dimethylformamide. Add 6.6 g of 7-amino-3-chloro cephalosporanic acid para-nitrobenzyl ester.

Leave to react overnight at room temperature; dilute with 150 mlit of ethyl acetate and wash repeatedly with water to extract all the DMF. Decolour the solution with 1 g of carbon, filter, and wash with acetate. Evaporate the rich phase in a vacuum until an oil is obtained, and dilute with 200 mlit of absolute ethanol.

Heat up to complete dissolution and then leave to cool down until precipitation of the product. Filter and wash with methanol and dry until constant weight is achieved. In this way, 10.1 g of product are obtained having an HPLC purity of 97.8%.

Melting point, 177° C. (decomposition) $^1$H NMR (DMSO D6 ISTD=tetramethylsilane) 9.93/9.90 (1H, d); 8.28/8.25 (2H, d); 7.74/7.71 (2H, d); 7.35/7.25 (17H, m); 6.11/6.07 (1H, dd); 5.49 (2H, s); 5.37/5.35 (1H, d); 4.08/3.75 (2H, AB).

EXAMPLE 5

Preparation of 7-β-[ (Z)-2-aminothiazolyl-5-chloro-α-trityloximino acetamide]-3-methoxymethyl cephalosporanic acid sodium salt Suspend 100 g of 3-methoxymethyl-7-amino-cephalosporanic acid in a mixture consisting of 2.1 lit of DMF and 300 muit of water. Add 270 g of thioester obtained according to Example 1 or Example 2, and then allow 68 mlit of TEA to drip over a period of 1 hour. Leave to react overnight at room temperature. At the end of the reaction, dilute with 2 lit of ethyl acetate and 1.5 lit of salt-saturated water. Bring the pH down to 3 with hydrochloric acid, separate the phases and wash the organic phase more than 3 times with 1 lit of salt water each time.

Evaporate the organic phase in a vacuum until the residue is obtained. Dilute with 1 lit of ethyl acetate and add 68 g of sodium 2-ethyl hexanoate; the sodium salt of the product precipitates immediately. Filter and wash with ethyl acetate.

After drying, 265 g of product are obtained having an HPLC purity of 98.5%.

Melting point, 180° (decomposition) $^1$H NMR (DMSO D6 18 TD tetranethylsilane) 9.92/9.90 (1H, d); 7.31/7.23 (17H, m); 5.95/5.91 (1H, dd); 5.24/5.23 (1H, d); 4.2 (2M, s); 3.64/3.46 (2H, AB); 3.2 (3H, s).

What is claimed is:

1. An aminothiazole compound of formula

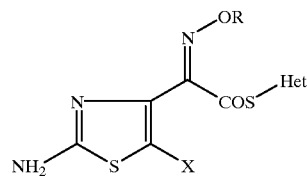

where:
X is a halogen;
Het is a 5- or 6-membered heterocyclic ring having in the ring at least one hetero-atom chosen from the group made up of N, S and O, either just as it is or condensed with a benzene ring;

R is H, $C_1$-$C_4$ alkyl, —$CH_2$—COOH or $C(CH_3)_2$—COOH, the acid functions of which are free, salified or esterified, $CH_2$—CN, $CH_2CF_3$, $CH_2F$,

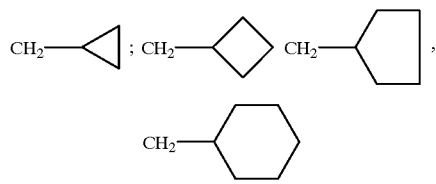

or a protective group of the easily removable type which is chosen from among the group consisting of trityl (Tr), tetrahydropyranyl (THP), tert-butyldimethylsilyl (TBDMS), trimetylsilyl (TMS), and methoxymethyl (MOM).

2. A compound according to claim 1, where X is Cl.

3. A compound according to claim 1, where Het is chosen from among the group consisting of

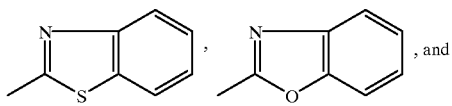, and

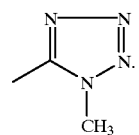

4. A compound according to claim 2, where R is chosen from among the group consisting of trityl (Tr), tetrahydropyranyl (THP), tert-butyldimethylsilyl (TBDMS), trimethylsilyl (TMS), and methoxymethyl (MOM).

5. A compound according to claim 2 where Het is chosen from among the group consisting of

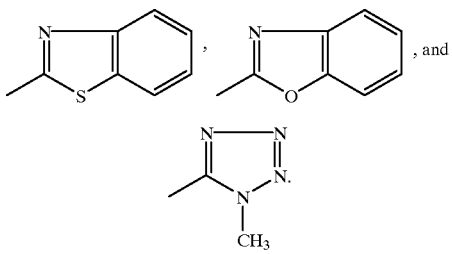

\* \* \* \* \*